Figure 1:
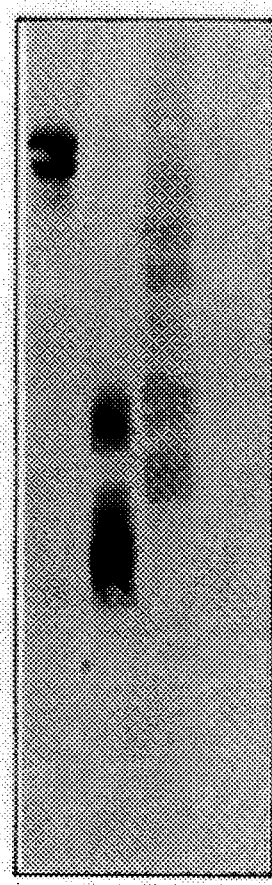

United States Patent [19]

Bouma et al.

[11] Patent Number: 5,656,484

[45] Date of Patent: Aug. 12, 1997

[54] PROTEIN S DELETION VARIANTS DEFICIENT IN C4BP BINDING ACTIVITY BUT HAVING APC COFACTOR ACTIVITY COMPOSITIONS AND THERAPEUTIC METHODS

[75] Inventors: Bonno Nammen Bouma, Hilversumsestraatweg 15, NL-3744 KB Baarn; Rogier Maria Bertina, Leiden, both of Netherlands

[73] Assignees: Rijksuniversiteit Leiden, Leiden; Bonno Nammen Bouma, Baarn, both of Netherlands

[21] Appl. No.: 436,804

[22] Filed: May 5, 1995

Related U.S. Application Data

[62] Division of Ser. No. 267,387, Jun. 29, 1994.

[30] Foreign Application Priority Data

Jun. 30, 1993 [EP] European Pat. Off. .............. 93201906

[51] Int. Cl.$^6$ ........................... C12N 1/21; C12N 15/63; C07H 21/04
[52] U.S. Cl. ........................ 435/252.3; 435/320.1; 536/23.5
[58] Field of Search ..................... 536/23.5; 435/320.1, 435/252.3

[56] References Cited

U.S. PATENT DOCUMENTS

| | | | |
|---|---|---|---|
| 5,321,123 | 6/1994 | Griffin et al. | 530/300 |
| 5,405,946 | 4/1995 | Griffin et al. | 530/380 |

OTHER PUBLICATIONS

Nelson, R., et al., "Binding of Protein S to C4b-binding Protein", *The Journal of Biological Chemistry*, vol. 267, No. 12, 1992, pp. 8140–8145.

Hong, J.C. et al. (1987) "Characterization and sequence analysis of a developmentally regulated putative cell wall protein gene isolated from soybean" *J. Biol. Chem* 262(17):8367–8376.

Chang, C.C. (1992) "Structure and function of human protein S" *Diss. Abstr. Int'l.* 54(02–C):528.

Chang, G.T.G. et al. (1991) "The carboxy terminal of human protein S is involved in the interaction with human C4b-binding protein" *Blood* 78(10, Suppl. 1):277a.

Gershagen, S. et al. (1991) "The genes for SHBG/ABP and the SHBG-like region of vitamin K-dependent protein S have evolved from a common ancestral gene" *J. Ster. Biochem. Molec. Biol.* 40(4–6):763–769.

*Primary Examiner*—Robert A. Wax
*Assistant Examiner*—Kawai Lau
*Attorney, Agent, or Firm*—Young & Thompson

[57] ABSTRACT

The present invention relates to various functional variants of recombinant protein S (PS) that do not significantly bind C4b binding protein (C4BP) and uses of the variants as a therapeutic reagent. In particular the invention is directed at deletion mutants of protein S, having cofactor activity toward APC and lacking at least the two postulated C4BP binding domains of the SHBG-like domain of the corresponding mature wild type protein S. Such a deletion mutant in particular lacks at least amino acid residues 401–457 and 583–635 of the corresponding mature wild type human protein S.

5 Claims, 5 Drawing Sheets

Binding of mini protein S to C4BP

Immuno analysis of mini protein S

Fig-5

PRIMARY STRUCTURE OF HUMAN PROTEIN S

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 3290 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CTGGCGCGCC  GCGCAGCACG  GCTCAGACCG  AGGCGCACAG  GCTCGCAGCT  CCGGGCGCCT      60

AGCTCCGGTC  CCCGCCGCGA  CGCGCCACCG  TCCCTGCCGG  CGCCTCCGCG  GCTCTCGAAA     120

TGAGGGTCCT  GGGTGGGCGC  TGCGGGGCGC  CGCTGGCGTG  TCTCCTCCTA  GTGCTTCCCG     180

TCTCAGAGGC  AAACCTTCTG  TCAAAGCAAC  AGGCTTCACA  AGTCCTGGTT  AGGAAGCGTC     240

GTGCAAATTC  TTTACTTGAA  GAAACCAAAC  AGGGTAATCT  TGAAAGAGAA  TGCATCGAAG     300

AACTGTGCAA  TAAAGAAGAA  GCCAGGGAGG  TCTTTGAAAA  TGACCCGGAA  ACGGATTATT     360

TTTATCCAAA  ATACTTAGTT  TGTCTTCGCT  CTTTTCAAAC  TGGGTTATTC  ACTGCTGCAC     420

GTCAGTCAAC  TAATGCTTAT  CCTGACCTAA  GAAGCTGTGT  CAATGCCATT  CCAGACCAGT     480

GTAGTCCTCT  GCCATGCAAT  GAAGATGGAT  ATATGAGCTG  CAAAGATGGA  AAAGCTTCTT     540

TTACTTGCAC  TTGTAAACCA  GGTTGGCAAG  GAGAAAAGTG  TGAATTTGAC  ATAAATGAAT     600
```

```
GCAAAGATCC CTCAAATATA AATGGAGGTT GCAGTCAAAT TTGTGATAAT ACACCTGGAA    660
GTTACCACTG TTCCTGTAAA AATGGTTTTG TTATGCTTTC AAATAAGAAA GATTGTAAAG    720
ATGTGGATGA ATGCTCTTTG AAGCCAAGCA TTTGTGGCAC AGCTGTGTGC AAGAACATCC    780
CAGGAGATTT TGAATGTGAA TGCCCCGAAG GCTACAGATA TAATCTCAAA TCAAAGTCTT    840
GTGAAGATAT AGATGAATGC TCTGAGAACA TGTGTGCTCA GCTTTGTGTC AATTACCCTG    900
GAGGTTACAC TTGCTATTGT GATGGGAAGA AAGGATTCAA ACTTGCCCAA GATCAGAAGA    960
GTTGTGAGGT TGTTTCAGTG TGCCTTCCCT GAACCTTGA CACAAAGTAT GAATTACTTT   1020
ACTTGGCGGA GCAGTTTGCA GGGGTTGTTT ATATTTAAA ATTTCGTTTG CCAGAAATCA   1080
GCAGATTTTC AGCAGAATTT GATTTCCGGA CATATGATTC AGAAGGCGTG ATACTGTACG   1140
CAGAATCTAT CGATCACTCA GCGTGGCTCC TGATTGCACT TCGTGGTGGA AAGATTGAAG   1200
TTCAGCTTAA GAATGAACAT ACATCCAAAA TCACAACTGG AGGTGATGTT ATTAATAATG   1260
GTCTATGGAA TATGGTGTCT GTGGAAGAAT TAGAACATAG TATTAGCATT AAAATAGCTA   1320
AAGAAGCTGT GATGGATATA AATAAACCTG GACCCCTTTT TAAGCCGGAA AATGGATTGC   1380
TGGAAACCAA AGTATACTTT GCAGGATTCC CTCGGAAAGT GGAAAGTGAA CTCATTAAAC   1440
CGATTAACCC TCGTCTAGAT GGATGTATAC GAAGCTGGAA TTTGATGAAG CAAGGAGCTT   1500
CTGGAATAAA GGAAATTATT CAAGAAAAAC AAAATAAGCA TTGCCTGGTT ACTGTGGAGA   1560
AGGGCTCCTA CTATCCTGGT TCTGGAATTG CTCAATTTCA CATAGATTAT AATAATGTAT   1620
CCAGTGCTGA GGGTTGGCAT GTAAATGTGA CCTTGAATAT TCGTCCATCC ACGGGCACTG   1680
GTGTTATGCT TGCCTTGGTT TCTGGTAACA ACACAGTGCC CTTTGCTGTG TCCTTGGTGG   1740
ACTCCACCTC TGAAAAATCA CAGGATATTC TGTTATCTGT TGAAAATACT GTAATATATC   1800
GGATACAGGC CCTAAGTCTA TGTTCCGATC AACAATCTCA TCTGGAATTT AGAGTCAACA   1860
GAAACAATCT GGAGTTGTCG ACACCACTTA AAATAGAAAC CATCTCCCAT GAAGACCTTC   1920
AAAGACAACT TGCCGTCTTG ACAAAGCAA TGAAAGCAAA AGTGGCCACA TACCTGGGTG   1980
GCCTTCCAGA TGTTCCATTC AGTGCCACAC CAGTGAATGC CTTTTATAAT GGCTGCATGG   2040
AAGTGAATAT TAATGGTGTA CAGTTGGATC TGGATGAAGC CATTTCTAAA CATAATGATA   2100
TTAGAGCTCA CTCATGTCCA TCAGTTTGGA AAAAGACAAA GAATTCTTAA GGCATCTTTT   2160
CTCTGCTTAT AATACCTTTT CCTTGTGTGT AATTATACTT ATGTTTCAAT AACAGCTGAA   2220
GGGTTTTATT TACAATGTGC AGTCTTTGAT TATTTTGTGG TCCTTTCCTG GGATTTTAA   2280
AAGGTCCTTT GTCAAGGAAA AAAATTCTGT TGTGATATAA ATCACAGTAA AGAAATTCTT   2340
ACTTCTCTTG CTATCTAAGA ATAGTGAAAA ATAACAATTT TAAATTTGAA TTTTTTTCCT   2400
ACAAATGACA GTTTCAATTT TTGTTTGTAA AACTAAATTT TTAATTTTAT CATCATGAAC   2460
TAGTGTCTAA ATACCTATGT TTTTTTCAGA AAGCAAGGAA GTAAACTCAA ACAAAAGTGC   2520
GTGTAATTAA ATACTATTAA TCATAGGCAG ATACTATTTT GTTATGTTT TTGTTTTTT    2580
CCTGATGAAG GCAGAAGAGA TGGTGGTCTA TTAAATATGA ATTGAATGGA GGGTCCTAAT   2640
GCCTTATTTC AAAACAATTC CTCAGGGGGA CCAGCTTTGG CTTCATCTTT CTCTTGTGTG   2700
GCTTCACATT TAAACCAGTA TCTTTATTGA ATTAGAAAAC AAGTGGGACA TATTTTCCTG   2760
AGAGCAGCAC AGGAATCTTC TTCTTGGCAG CTGCAGTCTG TCAGGATGAG ATATCAGATT   2820
AGGTTGGATA GGTGGGGAAA TCTGAAGTGG GTACATTTTT TAAATTTTGC TGTGTGGGTC   2880
ACACAAGGTC TACATTACAA AAGACAGAAT TCAGGGATGG AAAGGAGAAT GAACAAATGT   2940
GGGAGTTCAT AGTTTTCCTT GAATCCAACT TTTAATTACC AGAGTAAGTT GCCAAAATGT   3000
```

```
GATTGTTGAA GTACAAAAGG AACTATGAAA ACCAGAACAA ATTTTAACAA AAGGACAACC       3060

ACAGAGGGAT ATAGTGAATA TCGTATCATT GTAATCAAAG AAGTAAGGAG GTAAGATTGC       3120

CACGTGCCTG CTGGTACTGT GATGCATTTC AAGTGGCAGT TTTATCACGT TTGAATCTAC       3180

CATTCATAGC CAGATGTGTA TCAGATGTTT CACTGACAGT TTTAACAAT AAATTCTTTT        3240

CACTGTATTT TATATCACTT ATAATAAATC GGTGTATAAT CTAAAAAAAA                  3290
```

( 2 ) INFORMATION FOR SEQ ID NO:2:

( i ) SEQUENCE CHARACTERISTICS:
    ( A ) LENGTH: 635 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Ala Asn Ser Leu Leu Glu Glu Thr Lys Gln Gly Asn Leu Glu Arg Glu
1               5                   10                  15

Cys Ile Glu Glu Leu Cys Asn Lys Glu Ala Arg Glu Val Phe Glu
            20                  25                  30

Asn Asp Pro Glu Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
    50                  55                  60

Ala Tyr Pro Asp Leu Arg Ser Cys Val Asn Ala Ile Pro Asp Gln Cys
65                  70                  75                  80

Ser Pro Leu Pro Cys Asn Glu Asp Gly Tyr Met Ser Cys Lys Asp Gly
                85                  90                  95

Lys Ala Ser Phe Thr Cys Thr Cys Lys Pro Gly Trp Gln Gly Glu Lys
                100                 105                 110

Cys Glu Phe Asp Ile Asn Glu Cys Lys Asp Pro Ser Asn Ile Asn Gly
            115                 120                 125

Gly Cys Ser Gln Ile Cys Asp Asn Thr Pro Gly Ser Tyr His Cys Ser
    130                 135                 140

Cys Lys Asn Gly Phe Val Met Leu Ser Asn Lys Lys Asp Cys Lys Asp
145                 150                 155                 160

Val Asp Glu Cys Ser Leu Lys Pro Ser Ile Cys Gly Thr Ala Val Cys
                165                 170                 175

Lys Asn Ile Pro Gly Asp Phe Glu Cys Glu Cys Pro Glu Gly Tyr Arg
                180                 185                 190

Tyr Asn Leu Lys Ser Lys Ser Cys Glu Asp Ile Asp Glu Cys Ser Glu
            195                 200                 205

Asn Met Cys Ala Gln Leu Cys Val Asn Tyr Pro Gly Gly Tyr Thr Cys
    210                 215                 220

Tyr Cys Asp Gly Lys Lys Gly Phe Lys Leu Ala Gln Asp Gln Lys Ser
225                 230                 235                 240

Cys Glu Val Val Ser Val Cys Leu Pro Leu Asn Leu Asp Thr Lys Tyr
                245                 250                 255

Glu Leu Leu Tyr Leu Ala Glu Gln Phe Ala Gly Val Val Leu Tyr Leu
            260                 265                 270

Lys Phe Arg Leu Pro Glu Ile Ser Arg Phe Ser Ala Glu Phe Asp Phe
    275                 280                 285

Arg Thr Tyr Asp Ser Glu Gly Val Ile Leu Tyr Ala Glu Ser Ile Asp
    290                 295                 300
```

| | | | | | | | | | | | | | | |
|---|---|---|---|---|---|---|---|---|---|---|---|---|---|---|
| His 305 | Ser | Ala | Trp | Leu | Leu 310 | Ile | Ala | Leu | Arg | Gly 315 | Lys | Ile | Glu | Val 320 |
| Gln | Leu | Lys | Asn | Glu 325 | His | Thr | Ser | Lys | Ile 330 | Thr | Thr | Gly | Gly | Asp 335 | Val |
| Ile | Asn | Asn | Gly 340 | Leu | Trp | Asn | Met | Val 345 | Ser | Val | Glu | Glu 350 | Leu | Glu | His |
| Ser | Ile | Ser 355 | Ile | Lys | Ile | Ala | Glu 360 | Ala | Val | Met | Asp 365 | Ile | Asn | Lys |
| Pro | Gly 370 | Pro | Leu | Phe | Lys | Pro 375 | Glu | Asn | Gly | Leu | Leu 380 | Glu | Thr | Lys | Val |
| Tyr 385 | Phe | Ala | Gly | Phe | Pro 390 | Arg | Lys | Val | Glu | Ser 395 | Glu | Leu | Ile | Lys | Pro 400 |
| Ile | Asn | Pro | Arg | Leu 405 | Asp | Gly | Cys | Ile | Arg 410 | Ser | Trp | Asn | Leu | Met 415 | Lys |
| Gln | Gly | Ala | Ser 420 | Gly | Ile | Lys | Glu 425 | Ile | Ile | Gln | Glu | Lys 430 | Gln | Asn | Lys |
| His | Cys | Leu 435 | Val | Thr | Val | Glu | Lys 440 | Gly | Ser | Tyr | Tyr | Pro 445 | Gly | Ser | Gly |
| Ile | Ala 450 | Gln | Phe | His | Ile | Asp 455 | Tyr | Asn | Asn | Val | Ser 460 | Ser | Ala | Glu | Gly |
| Trp 465 | His | Val | Asn | Val | Thr 470 | Leu | Asn | Ile | Arg | Pro 475 | Ser | Thr | Gly | Thr 480 | Gly |
| Val | Met | Leu | Ala | Leu 485 | Val | Ser | Gly | Asn | Asn 490 | Thr | Val | Pro | Phe | Ala 495 | Val |
| Ser | Leu | Val | Asp 500 | Ser | Thr | Ser | Glu | Lys 505 | Ser | Gln | Asp | Ile | Leu 510 | Leu | Ser |
| Val | Glu | Asn 515 | Thr | Val | Ile | Tyr | Arg 520 | Ile | Gln | Ala | Leu | Ser 525 | Leu | Cys | Ser |
| Asp | Gln 530 | Gln | Ser | His | Leu | Glu 535 | Phe | Arg | Val | Asn | Arg 540 | Asn | Asn | Leu | Glu |
| Leu 545 | Ser | Thr | Pro | Leu | Lys 550 | Ile | Glu | Thr | Ile | Ser 555 | His | Glu | Asp | Leu | Gln 560 |
| Arg | Gln | Leu | Ala | Val 565 | Leu | Asp | Lys | Ala | Met 570 | Lys | Ala | Lys | Val | Ala 575 | Thr |
| Tyr | Leu | Gly | Gly 580 | Leu | Pro | Asp | Val | Pro 585 | Phe | Ser | Ala | Thr | Pro 590 | Val | Asn |
| Ala | Phe | Tyr 595 | Asn | Gly | Cys | Met | Glu 600 | Val | Asn | Ile | Asn | Gly 605 | Val | Gln | Leu |
| Asp | Leu 610 | Asp | Glu | Ala | Ile | Ser 615 | Lys | His | Asn | Asp | Ile 620 | Arg | Ala | His | Ser |
| Cys 625 | Pro | Ser | Val | Trp | Lys 630 | Lys | Thr | Lys | Asn | Ser 635 | | | | | |

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CAGAAGAGTT GTGAGTAAGT TTCAGTGTGC CTTCCC    36

PROTEIN S DELETION VARIANTS DEFICIENT IN C4BP BINDING ACTIVITY BUT HAVING APC COFACTOR ACTIVITY COMPOSITIONS AND THERAPEUTIC METHODS

This application is a division of application Ser. No. 08/267,387 filed Jun. 29, 1994, now pending.

TECHNICAL FIELD

The present invention relates to various functional variants of recombinant protein S (PS) that do not significantly bind C4b binding protein (C4BP) and uses of the variants as a therapeutic reagent.

BACKGROUND

Protein S (PS) is a vitamin K-dependent protein of 75,000 molecular weight with 635 amino acid residues. DiScipio et al., *Biochem.*, 18:899 (1979); Lundwall et al., *Proc. Natl. Acad. Sci. USA*, 83:6716–6720 (1986); Hoskins et al., *Proc. Natl. Acad. Sci. USA*, 84:394–353 (1987). Human plasma contains 346 nM PS of which 62% is complexed with the β chain subunit of complement protein, C4b binding protein (C4BP), and 38% is not complexed to C4BP and considered "free PS". Griffin et al., *Blood*, 79:3203–3211 (1992); Dahlback et al., *Proc. Natl. Acad. Sci. USA*, 78:2512 (1981); Dahlback et al., *J. Biol. Chem.*, 265:16082 (1990); and Nelson et al., *Biochemistry*, 30:2384 (1991).

PS exhibits anticoagulant activity in in vitro clotting assays. PS demonstrates anticoagulant cofactor activity for activated protein C (APC), an anticoagulant serine protease enzyme. Walker, *J. Biol. Chem.*, 255:5221–5224 (1980); Harris et al., *J. Biol. Chem.*, 260:2007 (1985); Stern et al., *J. Biol. Chem.*, 261:713 (1986); Walker, *J. Biol. Chem.*, 256:11128 (1981); and Solymoss et al., *J. Biol. Chem.*, 263:14884 (1988). PS has also been shown to be an anticoagulant factor in the absence of APC as it can inhibit prothrombinase activity in assays free of APC (Mitchell et al., *Thromb. Haemost.*, 60:298–304, 1988), and binds to Factor Va or Factor Xa and functions as an anticoagulant without APC. Heeb et al., *Circulation*, 86:3238a, 1992; and Heeb et al., *Circulation*, 86:1040a, 1992. In plasma, PS reversibly associates with C4BP with high affinity (dissociation constant of about 1–5 nanomolar). Only free PS is active as an APC cofactor and it is widely accepted that the association of PS with C4BP is associated with loss of the anticoagulant activity of PS. Dahlback, *J. Biol. Chem.*, 261:12022 (1986); and Taylor et al., *Blood*, 78:357–363 (1991). Therefore, C4BP is effectively an inhibitor of PS anticoagulant activity. The anticoagulant activity of PS can also be diminished or lost by cleavage at arginine residues within the so-called "thrombin-sensitive loop" comprising residues 46–75. Chang et al., *Circulation*, 86:3241a (1992).

PS is physiologically a very important antithrombotic factor since hereditary or acquired deficiencies of PS are associated with venous and arterial thrombotic disease. Allaart et al., *Thromb. Haemost.*, 64:206 (1990); Sie et al., *Thromb. Haemost.*, 62:1040 (1989); Engesser et al., *Ann. Intern. Med.*, 106–677 (1987); Mannucci et al., *Thromb. Haemost.*, 55:440 (1986); and Schwartz et al., *Blood*, 74:213 (1989). It is widely accepted that because only free PS has anticoagulant activity in vitro, the level of free PS in blood in vitro is considered the only relevant physiologic anticoagulantly active species. A deficiency of free PS with a normal level of total PS has been described in some patients with thrombotic disease (Comp et al., *Blood*, 67:504, 1986), and it has been hypothesized that an acquired deficiency of free PS due to temporary elevations of C4BP in disseminated intravascular coagulation or in a wide variety of inflammatory conditions, e.g. systemic lupus erythematosus, may contribute to s hypercoagulable state. Taylor et al., *Blood*, 78:357–363 (1991); Heeb et al., *Blood*, 73:455 (1989); Comp et al., *Blood*, 66:348a (1985); D'Angelo et al., *J. Clin. invest.*, 81:1445 (1988); Boerger et al., *Blood*, 69:692 (1987); and D'Angelo et al., *Ann. Intern. Med.*, 107:42 (1987). In addition, PS has been suggested to be important in metastasizing carcinoma and leukemias and therefore can be used therapeutically to inhibit cancer cell growth. Kemkes-Matthes, *Clin. Invest.*, 70:529–534 (1992).

Recently it was shown in an experimental primate animal model that elevations of C4BP exacerbate host response and convert a nonlethal dose of *E. coli* into a lethal dose. Taylor et al., *Blood*, 78:357–363 (1991). It was also shown that treatment of animals receiving excess PS with the C4BP did not suffer the lethal outcome or the hypercoagulable responses, thus showing that free PS which is not bound to C4BP may be a useful therapeutic agent for infection, inflammation and hypercoagulability. Taylor et al., *Blood*, 78:357–363 (1991). Furthermore, Schwarz et al., have described the use of plasma-derived PS in in vivo therapeutic methods for treating thrombosis and thromboembolic complications. U.S. Pat. No. 5,143,901.

Forms of PS that have reduced affinity for C4BP would provide useful therapeutic agents since they could be administered without risk of loss of activity associated with binding to C4BP.

In Chapter 3 of Glenn T. G. Chang's thesis "Structure and function of human protein S" of Dec. 11, 1992 two deletion variants of protein S are described and have been expressed in C127 cells. The E-variant has a deletion of the third epidermal growth factor like domain (deletion of exon VII corresponding to amino acid residues Asp-160–Asp-202) and expresses normal APC cofactor activity in a plasma system. This activity could be inhibited by the addition of purified C4BP, the binding affinity was similar to that exhibited by wild type.

The second variant (L-variant) which has a deletion of the C-terminal loop of the sex hormone binding globulin (SHBG)-like domain (deletion of exon XV, corresponding to amino acid residues Asp-583 to Ser-635) also expresses normal APC cofactor activity in plasma. This indicates that the third EGF-like domain and the C-terminal part of the SHBG-like domain of protein S are not involved in the expression of the APC cofactor activity of protein S.

The L-variant however shows reduced affinity for binding to C4BP. Due to the failure of monoclonal antibody S12 which recognizes a region close to Set 460 to bind to the nondenatured L-variant and the recognition of S12 by denatured L-variant, indicating the presence of the S12-epitope on the mutant, it is suggested by Chang that deletion of the C-terminal loop could induce a conformational change that results in a loss of binding affinity for C4BP at a binding site located outside the C-terminal loop of the protein S molecule and that loss of C4BP binding activity does not automatically imply that the C-terminal loop in particular Asp-583 to Serine 635 of the SHBG-like domain of protein S is involved in the interaction with C4BP. The numbering of the residues used by Chang is based on the numbering allocated in Dahlbäck, B., Lundwall, A., and Stenflo, J. (1986), *Proc. Natl. Acad. Sci. USA*, 78:2512–2516; Lundwall, A., Dackowski, W., Cohen, E. Shaffer, M. Math, A., Dahlbäck, B. Stenflo, J. and Wydro, R. (1986) *Proc.*

Natl. Acad. Sci. USA, 83:6716–6720; Hoskins, J., Norman, D. K., Beckman, R. J. and Long, G. L. (1987) Proc Natl. Acad. Sci. USA, 84:349–35 and Ploos van Amstel, H. K., Van der Zanden, A. L., Reitams, P. H. and Bertina, R. M. (1987) FEBS Lett. 222:186190.

In Fernández, J. A. and Griffin J. H. (1991) Thromb. Haemost 65:711 a C4BP binding site was reported in the center of the SHBG-domain, relatively close to amino acid residue Set-460 namely amino acid residues 420–434. As monoclonal antibody S12 itself does not interfere with the binding of C4BP to protein S this suggested that the S12 epitope and the Ser-460 region were not involved in the binding to C4BP.

In Chapter 4 of the aforementioned thesis Chang et al. describe mutants comprising substitutions of Glu 424 to Lys, Gln-427 to Glu and Lys-429 to Glu in the first disulfide loop. The latter mutant could not bind C4BP and could not recognize an anti-protein S antibody LJ-56 which inhibits complex formation of wild type protein S with C4BP. This confirmed that Lys-429 in the protein is involved in binding to C4BP and it may be concluded that both the first and second disulfide loop of the SHBG-like domain of protein S i.e. residues 408–434 and 598–635 respectively are involved in the interaction with C4BP.

Nelson and Long (Journ. of Biol. Chem. vol. 267, nr. 12, pages 8140–8145, Nelson, R. M. and Long, G. L.) illustrated that deletion of a greater part of the C-terminal loop between amino acid residues Tyr 577 to Ser 635 resulted in a reduced affinity for binding to C4BP, but this deletion leads to a protein without APC cofactor activity. A proper explanation for the lack of anticoagulant activity of Δ577–635 was its lack of full γ-carboxylation. The reason why Δ577–635 was not fully γ-carboxylated was not evident. Since the cells expressing the rHPS analog were not clonal, it could be a property of the severe truncation itself. While Δ577–635 was not able to function as a cofactor for APC, possibly due to having only about 8 of the usual 10–11 Gla residues and therefore being unable to interact optimally with $Ca^{2+}$, phospholipid, factor Xa and/or APC, it nevertheless binds to the $Ca^{2+}$-dependent monoclonal antibody used for its purification. This would argue that either the truncation itself directly impedes APC cofactor function, or that APC cofactor function is more stringent in its requirements for Gla than its antibody binding. While the latter seems the more likely explanation for the lack of anticoagulant activity of this mutant it is also a possibility that residues 577–607 confer upon protein S the proper configuration to enable APC cofactor function.

Surprisingly a deletion mutant lacking at least the postulated C4BP binding domain from residues 401–457 and the C4BP binding domain from 583–635 lacks C4BP binding activity but maintained APC cofactor activity. In fact even more surprisingly deletion of the complete C-terminal region known as the SHBG-like domain, i.e. deletion of approximately ⅔ of the wild type protein S without concomitant loss of APC cofactor activity of the resulting deletion mutant has been obtained. Residues 243–635 were removed without destroying the APC cofactor activity of the resulting mini protein S comprising residues 1–242 of the wild type protein S.

The subject invention is directed at a deletion mutant of protein S, having cofactor activity toward APC and lacking at least the two C4BP binding domains of the SHBG-like domain of the corresponding mature wild type protein S. Preferably the activity towards APC of the mutant protein S is no less than 95% of the activity illustrated by the corresponding mature wild type protein S from which the deletion mutant is derived.

In a preferred embodiment of the invention the deletion mutant is derived from human protein S. In the sequence id, listing 1 the amino acid sequence of wild type human protein S is given (SEQ ID No: 1). In sequence residues 1–37 comprise the Gla domain, residues 38–45 comprise the hydrophobic region, residues 46–75 comprise the thrombin sensitive domain, residues 76–242 comprise the 4 epidermal growth factor like domains and residues 243–635 comprise the SHBG like domain. There are two regions comprising disulfide loops situated within the SHBG like domain at residues 408–434 and 600–625. These two loops are postulated as being the C4BP domains necessary for protein S to bind C4BP as stated earlier in the specification. The invention is therefore in a particular embodiment directed at a deletion mutant human protein S lacking at least amino acid residues 408–434 and 600–625 of the corresponding mature wild type human protein S. A deletion mutant according to the invention can therefore have the amino acid sequence of sequence listing id 1, minus the deleted regions just indicated.

It is also possible for a deletion mutant according to the invention to not just miss the two small regions themselves but also to have a deletion of some or all of the interconnecting amino acid sequence. For human protein S this means a deletion from residue 408 to residue 625. It is also possible to have a deletion from the C-terminus to the end of the second C4BP domain seen from the C-terminal direction. For human protein S this means a deletion from residue 408 to the C-terminal residue. Even more surprisingly it has been discovered that even a deletion of the complete SHBG like domain leads to a deletion mutant that still possesses activity toward APC cofactor. Such a mutant in fact still possesses more than 95% of the activity toward APC that the mature wild type protein S possesses. This is extraordinary as the SHBG-like domain comprises two thirds of the mature wild type protein S and it is generally not expected that such a large deletion will not lead to conformational changes in the rest of the protein leading to inactivation.

The invention is therefore directed at a deletion mutant protein S that has at least a deletion of the C4BP domains and can also comprise further deletions of any size in the amino acid sequence of the SHBG like domain, including deletion of the complete SHBG like domain. For human mutant protein S this means an amino acid sequence according to id 1 comprising a deletion of at least amino acid residues 408–434 and 600–625 and optionally further comprising a deletion of any length in the remaining amino acid sequence located from amino acid residue 243 to the C-terminal amino acid residue leading to a deletion mutant human protein S according to the invention.

The invention describes a modified deletion mutant protein S, a mini protein S designated dPs, which has the desirable properties of:

(1) anticoagulant activity in in vitro coagulation assays; and (2) reduced ability to bind C4b binding protein (C4BP).

By anticoagulant activity is meant that the dPS has the ability to increase the clotting time of protein S deficient plasma in standard in vitro APC cofactor assays, preferably by at least 5%, more preferably by at least 10%, and still more preferably by at least from about 20 to 50%. Representative in vitro coagulation assays are described herein.

The ability of dPs of this invention to bind C4BP is measured in comparison to PS purified from human plasma, or PS produced by recombinant DNA methods, that is, wild-type PS. Preparation of plasma-purified PS has been described by Dahlback et al., *Biochem. J.*, 209:2007–2010 (1983), and by Schwartz et al., U.S. Pat. No. 5,143,901. (The teachings of all references cited are hereby incorporated by reference). Recombinant PS can be produced as described by Chang et al., *Thrombos. Haemost.*, 67:526–532 (1992), or as described herein. A reduced ability of dPS to bind C4BP when compared to wild-type human mature PS binding to C4BP can be any measurable decrease in binding in order to be useful according to this invention, because that reduced binding ability (expressed, for example, as a binding constant) translates into an increased resistance to neutralization by C4BP, an increased plasma level of free protein S, and therefore an effective increase in potency per unit weight of protein.

A preferred reduction in binding ability of C4BP is at least about 50%, preferably at least about 80%, and preferably at least about a 90 to 100% reduction in binding capacity, when measured in direct binding and expressed as a decrease in binding. Stated differently, dPs has less than about 50%, preferably less than 20% to 0% of the C4BP binding capacity of wild-type human mature PS when compared in equivalent C4BP binding assays. Binding of dPS can be measured by a variety of means known to a person skilled in the art.

A dPS of this invention is preferably substantially homologous to the corresponding part of the amino acid sequence encoding wild-type mature PS.

Because dPS is to be used, at least in one embodiment, in methods of treatment in vivo, it is important to present to the patient a protein substantially homologous to the native (wild-type) human PS as to limit possible deleterious immune responses to the protein. By substantially homologous is meant at least 95%, preferably at least 98%, and more preferably at least 99%, of the amino acid residues are the same as in wild-type human mature PS of the corresponding part of the amino acid sequence encoding wild type human mature PS, thereby minimizing the overall differences of the dPS relative to wild-type PS when viewed by the immune system.

The complete amino acid residue sequence of mature wild-type human PS is shown in SEQ ID NO 1. Mature PS refers to the protein after cleavage and removal of the leader polypeptide and signal sequence.

Insofar as protein S from species other than human are highly related both structurally and in terms of primary sequence, the invention also contemplates mutant protein S having the characteristics of dPS which are derived from other mammals, including cow, rat, rabbit, mouse, pig, primates, and the like.

It would obviously be advantageous to produce a mutant protein S not only having cofactor activity for APC and lacking C4BP binding activity but also being resistant to thrombin, as thrombin is known to cleave and inactivate wild type protein S. The invention is therefore also preferably directed at deletion mutants in the various embodiments just described further comprising at least one mutation in the thrombin sensitive loop region of the Gla domain of the corresponding mature wild type protein S, said mutation rendering the deletion mutant thrombin resistant.

It has been described by Chang et al, *Circulation*, 86:3241a (1992), that PS can be mutated at certain arginine residues, namely residues 49, 60 and 70 of wild-type PS, to reduce or eliminate the susceptibility of PS to proteolytic cleavages by thrombin which cause loss of anticoagulant activity. Thrombin-sensitive cleavage sites on PS have been identified to reside at residue positions 49, 60 and 70 in the thrombin sensitive loop region, or T-loop region. Thus, substitutions in this region define a class of mutations referred to as T-loop mutations that form a modified PS. Substitutions of one or more of the residues in the T-loop has been shown to reduce PS susceptibility to thrombin in vitro. Insofar as thrombin cleavage of PS inactivates the anticoagulant activity of PS, inhibition of thrombin sensitivity increases PS activity by increasing its serum half-life. Although the T-loop mutations do not appear to affect the binding of PS to C4BP, mutations in the T-loop do increase resistance to thrombin.

Therefore the subject invention is also directed at a deletion mutant of human protein S as described in the previous paragraph further comprising at least one mutation in the thrombin sensitive loop located in the region defined by residues 46 to 75 of the corresponding mature wild type human protein S. Preferably the mutation in the thrombin sensitive loop is a substitution mutation. Suitable mutation locations in the thrombin sensitive loop are residues at position 49, 60 and 70 of the amino acid sequence of the corresponding wild type mature human protein S.

Thus, the invention contemplates in another embodiment, a deletion mutant PS in which a further mutation comprises substitution of one or more of PS amino acid residue position numbers 49, 60 or 70.

Multiple substitutions are preferred over single substitutions at conferring thrombin resistance. Preferred substitutions are those selected from the group consisting of R49L, R60L and R70I. Particularly preferred substitutions are selected from the group consisting of R49L/R60L, R49L/R70I, R60L/R70I and R49L/R60L/R70I. The triple mutant is most preferred.

Thus a preferred dPS of this invention has a sequence comprising both (1) deletions of the regions responsible for C4BP binding, e.g., amino acid residue positions 401–457 and 583–635 or a deletion of residues 243-C terminal residue, and (2) substitutions in the T-loop region as recited herein. Thus a preferred dPS has one or more substitutions in the thrombin sensitive loop, in addition to at least the deletions of the C4BP binding regions as defined herein.

Another embodiment of the subject invention comprises a further mutation, said further mutation being located in the region comprising epidermal growth factor like domains 3 and 4 in the corresponding wild type mature protein S, preferably in human protein S. Such a mutation can be a substitution or deletion mutant. It is known from Dahlback et al. 1990c (Dahlback, B., Hildebrand, B., Malm J., Characterization of functionally important domains in human vitamin K-dependent protein S using monoclonal antibodies, *J. Biol. Chem.* 1990c; 265:8127–8135) that EGF1 and EGF2 are required for APC cofactor activity. As EGF 3 and EGF4 are not required it is possible in addition to the previously mentioned embodiments of the invention to include deletion mutants also lacking the EGF3 and EGF4 domains, i.e. in the region comprised in residues 160–242.

Any deletion mutants according to the invention just described can also undergo any further modifications, i.e. additions, deletions or substitutions that do not decrease the APC cofactor activity. For example it could be possible to make a fusion protein to combine desired characteristics of another protein or polypeptide with the interesting characteristics of the subject deletion mutant.

A deletion mutant protein S (dPS) according to the present invention is used, as discussed further herein, in a variety of therapeutic methods. A dPS can be formulated in pharmaceutical compositions, and can be administered to inhibit coagulation and other PS-mediated processes.

The invention is also directed at a synthetic or recombinant nucleotide sequence encoding an embodiment of a deletion mutant according to the invention and also covers a recombinant vector comprising such a nucleotide sequence, said vector preferably being capable of expressing said nucleotide sequence. The invention also covers a host cell comprising such a nucleotide sequence and/or comprising such a recombinant vector, said host cell preferably being capable of secreting the expression product encoded on said nucleotide sequence or on said vector.

A nucleotide sequence of the present invention is characterized as including a DNA sequence that encodes a deletion mutant protein S (dPS) according to the present invention. That is, a DNA segment of the present invention is characterized by the presence of a dPS structural gene. Preferably the gene is present as an uninterrupted linear series of codons where each codon codes for an amino acid residue found in the dPS protein, i.e. a gene free of introns.

One preferred embodiment is a nucleotide sequence that encodes an amino acid residue sequence that defines a dPS corresponding in sequence to a wild-type PS protein except that the amino acid residue sequence has at least two deletions of the amino acid sequence comprising the two C4BP binding sites, residues 401–457 and 583–635 and preferably a deletion of residues 243-C terminal residue, said nucleotide sequence preferably being capable of expressing a dPS.

A preferred nucleotide sequence codes for an amino acid residue sequence consisting essentially of the sequence shown in SEQ ID NO: 2 in which the aforementioned deletions of 401–457 and 583–635 are not present. A DNA sequence corresponding to amino acid sequence id2 is sequence id1. The PS nucleotide sequence id1 is also listed in Gen Bank having accession number Y00692. After post translation processing the corresponding amino acid sequence id2 is obtained. This amino acid residue sequence is also listed in Gen Bank having the accession number A26157.

In a related embodiment, such a nucleotide sequence further contains at least one of the substitutions selected from the group consisting of R49L, R60L and R70I, and the nucleotide sequence is capable of expressing a dPS. A particularly preferred nucleotide sequence includes nucleotide sequences that code for a dPS having substitutions selected from the group consisting of R49L/R60L, R49L/R70I, R60L/R70I and R49L/R60L/R70I. In other words, in one embodiment a nucleotide sequence codes for a dPS having deletions of at least both the C4BP binding domains and substitutions in the T-loop, as described herein.

Homologous DNA and RNA sequences that encode the above dPS are also contemplated.

DNA segments (i.e. synthetic oligonucleotides) that encode dPS proteins can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

In addition, the invention contemplates a recombinant DNA molecule (rDNA) comprising at least a nucleotide sequence of this invention. A rDNA can be produced by operatively linking a vector to a nucleotide sequence of the present invention.

As used herein, the term "vector" refers to a DNA molecule capable of autonomous replication in a cell and to which another nucleotide sequence can be operatively linked so as to bring about replication of the attached segment. A vector capable of directing the expression of a dPS gene is referred to herein as an "expression vector".

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules.

Those vectors that include a procaryotic replicon can also include a procaryotic promoter capable of directing the expression (transcription and translation) of the dPS gene in a bacterial host cell, such as *E. coli*, transformed therewith. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR-329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pXT1 available from Stratagene (La Jolla, Calif.), pJ5Eω) available from the American Type Culture Collection (ATCC; Rockville, Md.) as accession number ATCC 37722, pTDT1 (ATCC 31255), and the like eucaryotic expression vectors.

The invention also contemplates a host cell transformed with a recombinant DNA molecule of the present invention. The host cell can be either procaryotic of eucaryotic, although eucaryotic cells are preferred. Eucaryotic cells useful for expression of a dPS protein are not limited, so long as the cell line is compatible with cell culture methods and compatible with the propagation of the expression vector and expression of the dPS gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines. Particularly preferred and exemplary is the mouse mammary tumor cell line C127I described by Howley et al., *J. Virol.*, 26:291–298 (1978), and available from the ATCC as ATCC CRL 1616.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing rDNAs, see, for example, Graham et al.,

*Virol.*, 52:456 (1973); Wigler et al., *Proc. Natl. Acad. Sci. USA*, 76:1373–76 (1979), and the teachings herein.

Successfully transformed cells, i.e., cells that contain a rDNA molecule of the present invention, can be identified by well known techniques, such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of dPS, or by the detection of the biological activity of dPS.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying dPS antigenicity or biological activity.

Nutrient media useful for culturing transformed host cells are well known in the art and can be obtained from several commercial sources. In embodiments wherein the host cell is mammalian, a "serum-free" medium can be used. Preferred are the culturing conditions described herein.

Deletion mutant human protein S (dPS) of this invention can be produced by a variety of means, and such production means are not to be considered as limiting.

Preparation of a dPS typically comprises the steps of: providing a DNA segment that codes a dPS protein of this invention; introduction of the provided DNA segment into an expression vector; introduction of the vector into a compatible host cell; culturing the host cell under conditions sufficient for expression of the dPS protein; and harvesting the expressed dPS protein from the host cell.

Insofar as the expressed protein is highly related to wild-type PS, the purification of dPS can be conducted by a variety of art-recognized procedures for preparing purified PS from cell culture.

Thus, in one embodiment, a dPS protein is prepared using a nucleotide sequence as described herein. Alternatively, one can use the screening methods described herein to identify additional substitutions of amino acids in the wild-type PS which produce a dPS having the disclosed desirable properties. As seen by the numerous mutant constructs described herein, a variety of dPS proteins can be produced by the present methods. Additional substitutions (mutations) or deletions other than those described specifically herein can be readily designed to form a dPS having the disclosed biological activities. The mutations can be introduced by any of a variety of procedures, such as in vitro site-directed mutagenesis using preselected oligonucleotides.

Also contemplated are a pharmaceutical composition comprising at least a pharmaceutically acceptable carrier and a deletion mutant protein S according to the invention as active component. Use of a deletion mutant protein S according to the invention as such or as a pharmaceutical composition for treatment of any of the following: a patient at risk for acute thrombosis, protein S deficiency, sepsis, inflammation and cancer also fall within the scope of the invention.

A deletion mutant human protein S (dPS) of the invention is typically provided in one or more of a variety of compositional forms suitable for the contemplated use. Although dPS retains its biological activity in a variety of buffers and solutions, it is preferred to be formulated in a pharmaceutically acceptable excipient. Particularly preferred are compositions which afford maximum stability and biological activity of the dPS in the composition. Such compositions are generally well known in the art.

In one embodiment, a composition can further contain a therapeutically effective amount of a second active ingredient that is effective as an anticoagulant or thrombolytic agent.

Insofar as PS is a calcium dependent protein, preferred compositions further contain divalent calcium cations, typically in a physiological amount.

Therapeutic compositions of the present invention contain a physiologically tolerable carrier together with at least one species of dPS as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

In addition, a therapeutic composition is preferably pyrogen free, i.e., incapable of inducing a pyrogenic response when assayed in conventional assays for pyrogens.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of dPS can be present in an ointment or on a diffusible patch, such as a bandage, as to afford local delivery of the agent.

In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein.

A therapeutic composition contains an effective amount of dPS of the present invention, typically an amount of at least 0.1 weight percent of active protein per weight of total therapeutic composition. A weight percent is a ratio by weight of dPS protein to total composition.

In view of the demonstrated ability of dPS to act as an anticoagulant, coupled with the reduced or absent C4BP binding activity, a dPS of this invention has the ability to function as a useful anticoagulant with increased plasma levels of free PS due to its relative inability to be inactivated by C4BP. Thus, a dPS of this invention can be used therapeutically in place of wild-type protein S (PS) where PS might be used therapeutically. Typical applications for PS, and particularly a dPS of this invention, include coagulative processes in which PS can function to inhibit coagulation, and particularly those processes where C4BP would be present to inhibit PS.

A representative patient for practicing the present methods is any human at risk for thrombosis, inflammation or other deleterious biological processes in which wild-type PS would provide an ameliorative effect.

Exemplary coagulative processes of particular therapeutic importance for a therapeutic method using dPS include acute thrombosis (both venous and/or arterial), hereditary or acquired protein S deficiency, sepsis, inflammation processes, and cancer. The use of PS in arterial and venous thrombosis is particularly preferred, as indicated by several studies; Green, et al., *Neurology*, 42:1029 (1992); Thommen, et al., *Schenlz.med Wschr.*, 119:493–499 (1989); Wiesel, et al., *Thromb. Res.*, 58:461–468 (1990).

The method comprises contacting a tissue, organ, body fluid sample such as blood, plasma or serum, or the circulatory system of a patient, in vivo or in vitro, with a composition comprising a pharmaceutically effective amount of a dPS of this invention. In one embodiment, the contacting in vivo is accomplished by administering a therapeutically effective amount of a physiologically tolerable composition containing a dPS of this invention to a patient.

Thus, the present invention describes in one embodiment a method for inhibiting coagulation in a human comprising administering to the human a composition comprising a therapeutically effective amount of a dPS of this invention.

A therapeutically effective amount of a dPS is a predetermined amount calculated to achieve the desired effect, i.e., to reduce the coagulation time in the body fluid sample of the circulation of the patient, and thereby decrease the likelihood of coagulation. In the case of in vivo therapies, an effective amount can be measured by improvements in one or more symptoms associated with coagulation, inflammation, sepsis or protein S deficiency.

Thus, the dosage ranges for the administration of a dPS of the invention are those large enough to produce the desired effect in which the symptoms of coagulation are ameliorated or the likelihood of coagulation is decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an dPS of this invention is typically an amount such that when administered in a physiologically tolerable composition is sufficient to achieve a plasma or local concentration of from about 1 nanomolar (nM) to 1 micromolar (uM), preferably about 10 to 500 nM, and most preferably about 50 to 200 nM.

The dPS of the invention can be administered parenterally by injection or by gradual infusion over time. The dPS of the invention can be administered intravenously, intraperitoneally, intramuscularly, subcutaneously, intracavitally, transdermally, dermally, and can be delivered by peristaltic means. Because coagulation and inflammation are preferred targets for the present methods, intravenous administration to the circulation is a particularly preferred route.

Representative therapeutic methods, describing exemplary dosages and routes of administration, using PS that are applicable to the present methods using dPS, are described in U.S. Pat. No. 5,143,901 to Schwarz et al.

In a related embodiment, the invention contemplates the use of dPS in combination with other anticoagulation therapies. In particular, in view of PS as a cofactor to activated protein C (APC), a preferred embodiment utilizes dPS therapeutic compositions in combination with therapeutically effective amounts of protein C (PC) zymogen or APC. PC is known to be converted in vivo to APC, and can therefore be used in place of or in combination with APC in in vivo methods. Therefore, in one embodiment the invention contemplates a method of inhibiting coagulation comprising the administration of both a therapeutically effective amount of dPS and a therapeutically effective amount of PC, APC or both, each in a pharmaceutically acceptable excipient. A representative procedure using native PS and APC is described in U.S. Pat. No. 5,143,901 to Schwarz et al., as is the preparation of purified APC suitable for therapeutic use.

EXAMPLE construction of human mini protein S and analysis thereof.

A recombinant human protein S molecule that lacks the human sex hormone binding globulin (SHBG) like domain (mini protein S, residues 1–242) was constructed. The truncated molecule was expressed in a mammalian cell expression system, purified from the cell culture medium and characterized.

On reduced SDS polyacrylamide gel electrophoresis the molecular weight of mini protein S was assessed.

Using an activated partial thromboplastin time clotting assay system mini protein S was able to dose dependently enhance the activated protein C induced clotting time of protein S deficient plasma.

Furthermore, mini protein S was probed with a panel of anti-protein S monoclonal antibodies.

Finally, mini protein S did not interact with C4b-binding protein (C4BP) in a system using purified proteins, suggesting the binding site for C4BP to be localized in the SHBG-like domain.

Experimental Procedures

Materials—Restriction endonucleases BamH I, Xba I Bgl II and Hind III were purchased from Pharmacia Biotechnology (Uppsala, Sweden). T4 DNA Ligase was from Bethesda Research Laboratory (Bethesda, Mass., USA). All enzymes were used according to the manufacturers instructions. Echerichia coli strains CJ236 and XL-1 blue were from Bio-Rad (Richmond, Calif., USA). APC, protein S and C4BP depleted plasma was prepared as described (Koedam, J. A., Meijers, J. C. M., Sixma, J. J. and Bouma, B. N. (1988) *J. Clin. Invest.* 82, 1236–1243). C4BP and anti-C4BP monoclonal antibodies 8C11, directed against the α-chain of C4BP was prepared as described (Hessing, M., Vlooswijk, R. A. A., Hackeng, T., Kanters, D. and Bouma, B. N. (1990) *J. Immunol.* 144, 204–208). Rabbit anti human protein S IgG conjugated to peroxidase were from Dakopatts (Glostrup, Denmark). Monoclonal antibodies were prepared as described (Hackeng, T. M., Hessing, M., van 't Veer, C., Meijer-Huizinga, E., Meijers, J. C. M., De Groot, P. G., Van Mourik, J. A. and Bouma, B. N. (1993) *J. Biol. Chem.* vol 268, p3993–4000). Iscoves Dulbeccos Modified Medium, pennicillin, streptomycin sulphate, glutamine and fetal calf serum were from Gibco (Paisly Park, UK). Trasylol was from Bayer (Leverkusen, FRG). Vitamin $K_1$ (Konakion) was from F. Hoffman-La Roche (Basel, Switzerland). Vectastain ABC kit was obtained from Vector Laboratories, Burlingame, Calif., USA.

Site Directed Mutagenesis—A 2808-base pair Hind III-BamH I fragment from the expression vector pMSVPS (Chang, G. T. G., Ploos van Amstel, H. K., Hessing, M., Reitsma, P. H., Bertina, R. M. and Bouma, B. N. (1992) *Thromb. Haemost.* 67, 526–53221) carrying the Protein S cDNA sequence was subcloned into M13mp19 after digestion with Hind III and Bgl II. The following 36-mer was used as primer: 5'-CAG AAG AGT TGT GAG TAA GTT TCA GTG TGC CTT CCC-3 (SEQ ID NO: 3) to hybridize with the nucleotide sequence encoding the amino acid sequence between residues 238–249. The codon TAA at position 243 is a stop codon, therefore the recombinant protein is 242 amino acids long. Underlined nucleotides were altered. Site directed mutagenesis was performed according to Kunkel (Kunkel, T. A. (1985) *Proc. Natl. Acad. Sci. USA* 82, 488–492). The M13mp19 clone carrying the protein S insert was infected into CJ236 (dut⁻ung⁻) cells and uracil-containing single stranded phage DNA was isolated and used as template. After second strand synthesis with T7 DNA Polymerase and ligation with T4 DNA Ligase competent XL-1 blue (dut⁺ung⁺) cells were transformed. Single stranded DNA from individual resultant plaques was isolated and sequenced by the dideoxy chain termination method (Sanger, F., Nicklen, S. and Coulson, A. R. (1977) *Proc. Natl. Acad. Sci. USA* 76, 5463–5467) to confirm the sequence was as expected. Double-stranded phage DNA was isolated from bacterial cells and the protein S insert isolated, after Hind III and Xba I digestion and recloned into pMS-VPS. The BPV-1 genome was isolated after BamH I digestion of pTZX-BPV as described before (Chang, G. T. G., Ploos van Amstel, H. K., Hessing, M., Reitsma, P. H., Bertina, R. M. and Bouma, B. N. (1992) *Thromb. Haemost.* 67, 526–532) and cloned into pMSVPS. The resulting plasmid was purified by polyethylene glycol precipitation and deposited at the CBS in Baarn, the Netherlands on Jun. 24, 1993 under accession number 36193 in accordance with the Budapest Treaty.

Cell Culture, DNA transfection and Purification of Recombinant Mini Protein S—C127 cells (ATCC CRL 1616) were cultured as described before (Chang, G. T. G., Ploos van Amstel, H. K., Hessing, M., Reitsma, P. H., Bertina, R. M. and Bouma, B. N. (1992) *Thromb. Haemost.* 67, 526–532). For transfections 20 μg of plasmids were used and cells were transfected by conventional calcium phosphate coprecipitation technique (Graham, F. and van der Eb, A. (1983) *Virology* 52, 456–467). The conditioned medium containing recombinant protein S, as determined by an ELISA, was harvested after 48 h of expression in the presence of vitamin $K_1$ (Konakion, Roche, 5 μg/ml). Recombinant protein S was purified on an anion exchange column (Fast Flow Q resin, Pharmacia) as described (Chang, G. T. G., Ploos van Amstel, H. K., Hessing, M., Reitsma, P. H., Bertina, R. M. and Bouma, B. N. (1992) *Thromb. Haemost.* 67, 526–532). The purity and integrity of the recombinant protein S were judged after separation with SDS/PAGE on reduced 12.5% gels (Laemmli, U.K. (1970) *Nature* 227, 608–695) and immunoblotting (Towbin, H. J., Staehlin, T. and Gordon J. (1979) *Proc. Natl. Acad. Sci. USA* 76, 4350–435426) using rabbit anti-protein S polyclonal and mouse anti-protein S monoclonal antibodies.

Protein S Assays—Protein S antigen was determined using a specific monoclonal antibody ELISA. IgG of two independent anti-protein S monoclonal antibodies (13 and 3D9, 5 μg/ml each) were coated in 50 mM NaHCO₃, pH 9.6 overnight at 4° C. on to polyvinyl microtitre plates (Costar, Cambridge, Mass., USA).

After washing of unbound IgGs, the wells were blocked with 1% (w/v) BSA in 50 mM Tris-HCl pH 7.5 containing 150 mM NaCl and 5 mM CaCl₂ for 1 h at room temperature. Increasing amounts of recombinant protein S were added and incubated for 18 h at room temperature. Bound protein S was allowed to bind to anti-protein S monoclonal antibody 18 IgG conjugated to biotin (0.5 μg/ml) for 1 h. ABC reagent was added (100 μl) and incubated for 1 h at room temperature. The hydrolysis of nitrophenylphosphate was measured at 492 nm using a $V_{max}$ plate reader (Molecular Devices Corporation, Menlo Park, Calif., USA).

APC cofactor activity was determined in a clotting assay as described by Chang, G. T. G., Ploos van Amstel, H. K., Hessing, M., Reitams, P. H., Bertina, R. M. and Bouma, B. N. (1992) *Thromb. Haemost.* 67, 526–532).

Binding of Recombinant Protein S to C4BP—The complex formation between the recombinant protein S and C4BP was measured with a sensitive ELISA using C4BP and a biotin conjugated anti-protein S monoclonal antibody 18. Briefly, IgG (10 μg/ml) from monoclonal antibody 8C11, which is directed against the α-chain of C4BP was coated in 50 mM NaHCO₃, pH 9.6 overnight at 4° C. on to polyvinyl microtitre plates (Costar, Cambridge, Mass., USA). After washing of unbound IgGs, the wells were blocked with 1% (w/v) BSA in 50 mM Tris-HCl pH 7.5 containing 150 mM NaCl and 5 mM CaCl₂ for 1 h at room temperature and C4BP was allowed to bind for 2 h with a final concentration of 1 μg/ml. Increasing amounts of recombinant protein S were added and incubated for 18 h at room temperature. Bound protein S was allowed to bind to anti-protein S IgG monoclonal antibody 18 conjugated to biotin (0.5 μg/ml) as described earlier.

Inactivation of Protein S by Thrombin—One ml of recombinant protein S (50 μg/ml) was incubated with 50 μl of thrombin-Sepharose (1 mg/ml) for 1 h at 37° C. in 50 mM Tris-HCl pH 7.5 containing 150 mM NaCl. Thrombin-Sepharose was removed by centrifugation and inactivated protein S was stored at −20° C. until needed.

Binding of Mini Protein S to Anti-Protein S Monoclonal Antibodies—Recombinant or mini protein S (900 ng) were coated on to polyvinyl microtitre plates in 50 mM NaHCO₃, pH 9.6 overnight at 4° C. IgG of different monoclonal antibodies (0–1.5 μg/ml) were added and incubated for 2 h at room temperature. The hydrolysis of nitrophenyl phosphate was measured at 492 nm using a $V_{max}$ plate reader (Molecular Devices Corporation, Menlo Park, Calif., USA).

Results and Discussion

To study the role of the SHBG-like domain of protein S, mini protein S (residues 1–242) was constructed and was expressed in C127 cells. Foci producing recombinant mini protein S as determined by an ELISA were isolated and subcloned using 1 cell/well. The highest protein S producing clone was used for large-scale production of mini protein S. Mini protein S was purified from the culture medium using a Fast Flow Q column. On reduced SDS gels mini protein S had lower apparent molecular masses of 30 and 20 kD (FIG. 1). The upper band represented mature protein S (residues 1–242) and could be converted into the lower band by thrombin (residues 71–242).

Figure 2:
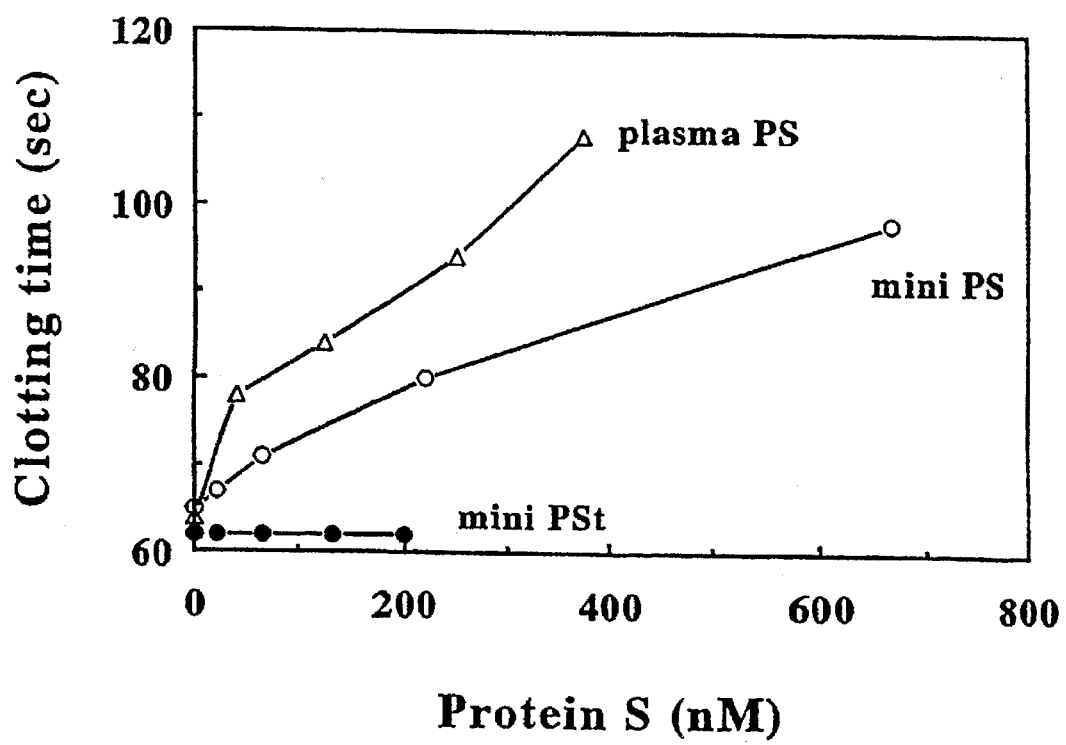

The cofactor activity for APC was measured in an activated partial thromboplastin time system using protein S and C4BP depleted plasma and increasing amounts of protein S. FIG. 2 demonstrates that mini protein S possesses cofactor activity to APC, which could be inhibited by thrombin. The cofactor activity was two-fold lower compared to wild type protein S on a molar basis. This could be due to the amount of cleaved material in the mini protein S preparation. At this stage mini protein S contained 80% cleaved material, whereas wild type protein S contained 50% (FIG. 1). This experiment further demonstrates that deletion of the SHBG-like domain does not effect the APC cofactor activity and shows that the interaction of protein S with APC probably occurs via the N-terminus as recently reported by Dahlback and coworkers using monoclonal antibodies and protein S fragments (Dahlbäck, B., Hildebrand, B. and Malm, J. (1990) *J. Biol. Chem.* 265, 8127–8135).

Binding of mini protein S to C4BP in the presence of calcium (FIG. 3) shows that the mini protein S does not bind to C4BP as the wild type recombinant protein S. This suggests that the SHBG-like domain contains the binding site for C4BP. It further suggests that the SHBG-like domain is probably not involved in the anticoagulant system, but more in the complement system.

Using the ELISA system (FIG. 4), antibody 18 recognized mini protein S equally well as wild type, whereas S7 did not recognize mini protein S. Monoclonal antibody 18 is directed against an epitope in the EGF3 and EGF4 region, whereas monoclonal antibody S7 is directed against an epitope in the SHBG region close to amino acid 460.

Legends to Figures

FIG. 1. SDS/PAGE analysis of immunoblotted protein S. Aliquots (100 ng) of recombinant protein S (lane 1) or mini protein S (lane 2) were separated on a 12.5% SDS gel under reducing conditions and immunoblotted onto immobilon membranes. Bound proteins were detected using rabbit anti-protein S polyclonal antibodies conjugated to peroxidase.

FIG. 2. Protein S cofactor activity to APC: effect of thrombin. The protein S dependent prolongation of the clotting time was measured in an activated partial thromboplastin time system using protein S and C4BP depleted plasma, APC, kaolin and cephalin. Increasing amounts of recombinant protein S (circles), or mini protein S (squares) treated without (open symbols) or with (closed symbols) thrombin were added. Clotting was initiated by the addition of $CaCl_2$ and the clotting time was measured. The experiment was performed in duplicate.

Figure 3:
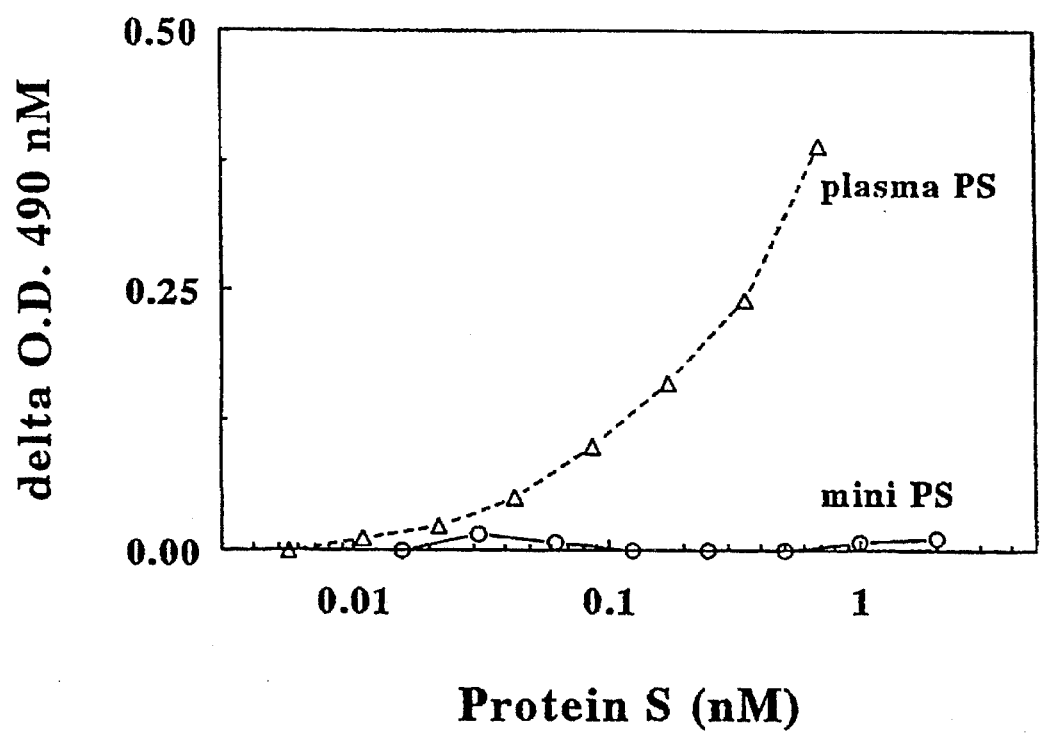

FIG. 3. Binding of mini protein S to C4BP. Anti-C4BP monoclonal antibody 8C11 IgG was coated onto microtitre wells to catch C4BP (1 µg/ml). Recombinant protein S (circles) or mini protein S (squares) were added in increasing amounts in the presence of calcium. Binding to C4BP was for 18 h at room temperature. Bound protein S was detected with anti-protein S 18 IgG conjugated to biotin (0.5 µg/ml). The experiment was performed in duplicate.

Figure 4:
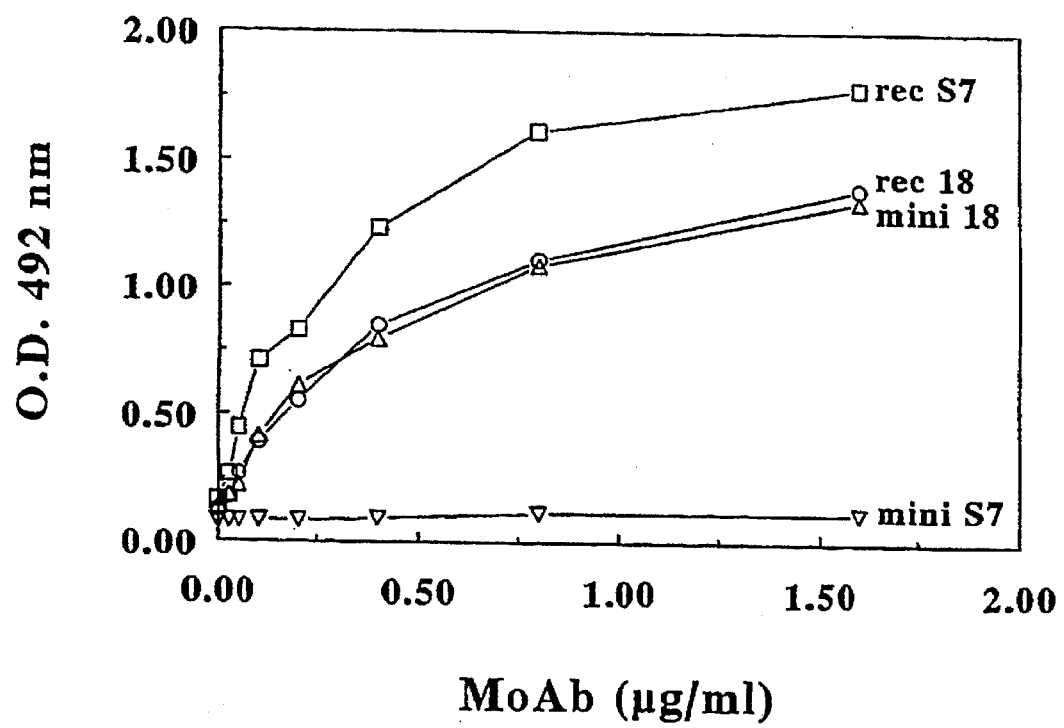

FIG. 4. Binding of mini protein S to different monoclonal antibodies. Microtitre plates were coated with a fixed amount of wild type recombinant (rec) ([ ], O) or mini protein S (mini) (Δ, V) and increasing amounts of different monoclonal antibodies S7 ([ ], V) or 18 (O, Δ) were added for 2 h at room temperature. Bound antibodies were measured using rabbit anti-mouse antibodies conjugated to peroxidase as described in "Experimental Procedures".

Figure 5:
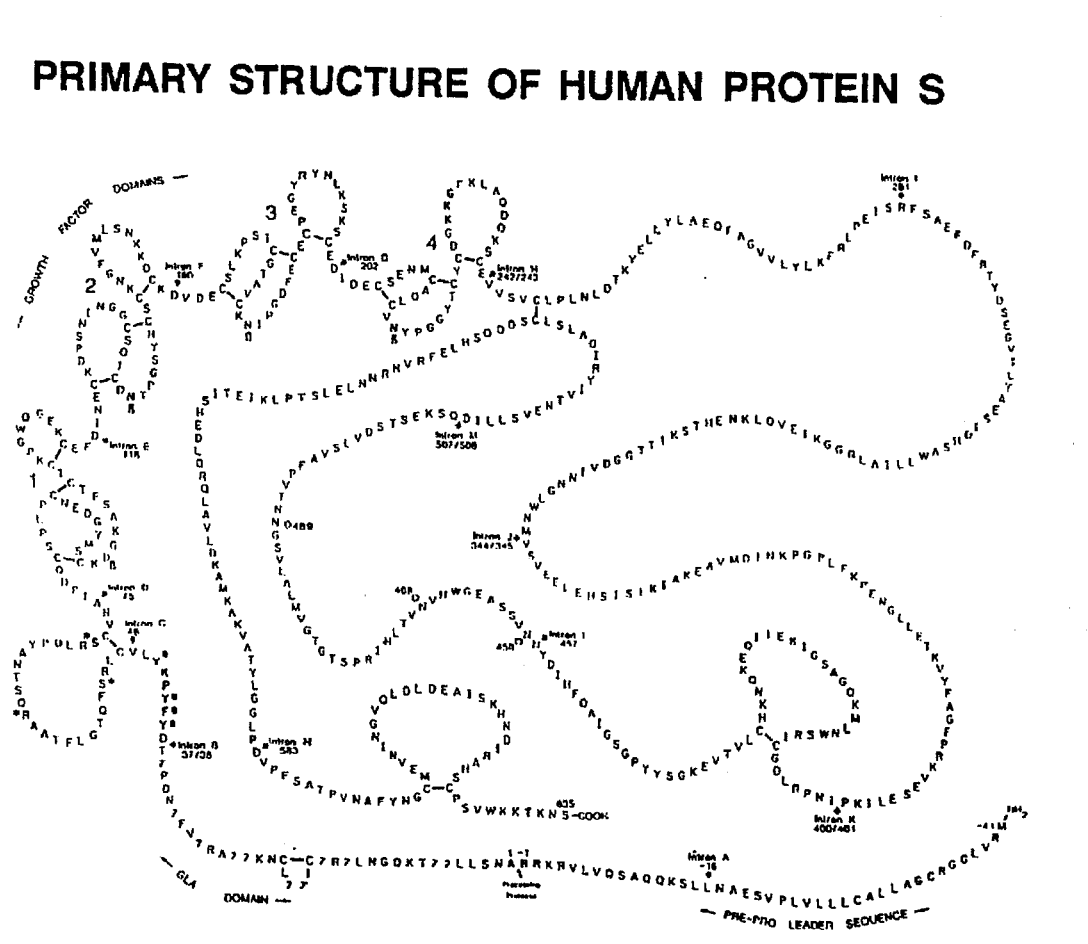

FIG. 5. Primary structure of human protein S. Amino acid sequence (one-letter code) for human prepro protein S and location of the 14 introns (A–N), indicated by solid arrows. The prepro leader sequence includes residues −41 to −1. Solid bars are disulfide bonds; γ, γ-carboxyglutamic acid (GLA); β, β-hydroxyaspartic acid or β-hydroxyasparagine; *, thrombin-cleavage site in the thrombin-sensitive domain; o, aromatic amino acid residues in the aromatic stack domain; open diamonds indicate potential carbohydrate attachment sites of the Asn-X-Ser/Tyr type. Large numbers denote orders of four epidermal growth factor-like domains, which are followed by the sex hormone binding globulin-like domain.

---

We claim:

1. A synthetic or recombinant nucleotide sequence encoding a deletion mutant of human protein S, having cofactor activity to activated protein C and having at least 95% amino acid residue sequence identity with wild type mature human protein S having the amino acid sequence shown in SEQUENCE ID NO: 2 comprising a deletion of any length in the part of the amino acid sequence located from amino acid residue 243 to the C terminal amino acid, said deletion comprising at least deletion of amino acid residues 408–434 and 600–625.

2. A recombinant vector comprising a nucleotide sequence according to claim 1, said vector being capable of expressing said nucleotide sequence.

3. A host cell comprising a nucleotide sequence according to claim 1, said host cell being capable of secreting the expression product encoded on said nucleotide sequence.

4. A host cell comprising a recombinant vector according to claim 2, said host cell being capable of secreting the expression product encoded on said vector.

5. A synthetic or recombinant nucleotide sequence encoding a deletion mutant of human protein S, having cofactor activity to activated protein C and having at least 95% amino acid residue sequence identity with wild type mature human protein S having the amino acid sequence shown in SEQUENCE ID NO: 2 comprising a deletion of the amino acid sequence located from amino acid residue 243 to the C terminal amino acid.

* * * * *